United States Patent [19]

Hussong

[11] Patent Number: 4,799,885
[45] Date of Patent: Jan. 24, 1989

[54] AUTOMATIC HIGH VELOCITY EVACUATOR DENTAL SUCTION DEVICE

[76] Inventor: Dean R. Hussong, 10 Bradley Farm Rd., Tomahawk, Wis. 54487

[21] Appl. No.: 56,422

[22] Filed: Jun. 1, 1987

[51] Int. Cl.$^4$ .............................................. A61C 17/04
[52] U.S. Cl. .................... 433/95; 200/61.86; 137/38
[58] Field of Search .................... 433/91, 92, 95, 96; 604/30, 31, 35, 36; 137/38, 39, 901; 251/65, 129.14; 200/61.47, 61.52, 61.86, 200, 224, 225

[56] References Cited

U.S. PATENT DOCUMENTS

| | | | |
|---|---|---|---|
| 1,882,154 | 10/1932 | Mann et al. | 141/286 |
| 2,056,322 | 10/1936 | Hoppe | 137/139 |
| 2,093,419 | 9/1937 | Coleman | 200/61.47 |
| 3,031,760 | 5/1962 | Bender | 433/27 |
| 3,218,624 | 11/1965 | Zane | 432/27 |
| 3,245,652 | 4/1966 | Roth | 251/139 |
| 4,043,033 | 8/1977 | Yeo | 29/739 |
| 4,081,176 | 3/1978 | Johnson | 433/95 |
| 4,340,365 | 7/1982 | Pisanu | 433/80 |
| 4,441,014 | 4/1984 | Hong | 219/240 |
| 4,489,863 | 12/1984 | Horchos et al. | 222/504 |
| 4,522,592 | 6/1985 | Johnson | 433/95 |
| 4,556,195 | 12/1985 | Calkins | 251/129.20 |

Primary Examiner—Larry Jones
Assistant Examiner—Noah Kamen
Attorney, Agent, or Firm—Allegretti & Witcoff, Ltd.

[57] ABSTRACT

An improved dental suction device is disclosed comprising a suction line and automatic, orientation-responsive switching means adapted to provide suction at the inlet when the device is aligned in a first operative orientation and turn off the suction at the inlet when aligned in a second standby orientation.

5 Claims, 1 Drawing Sheet

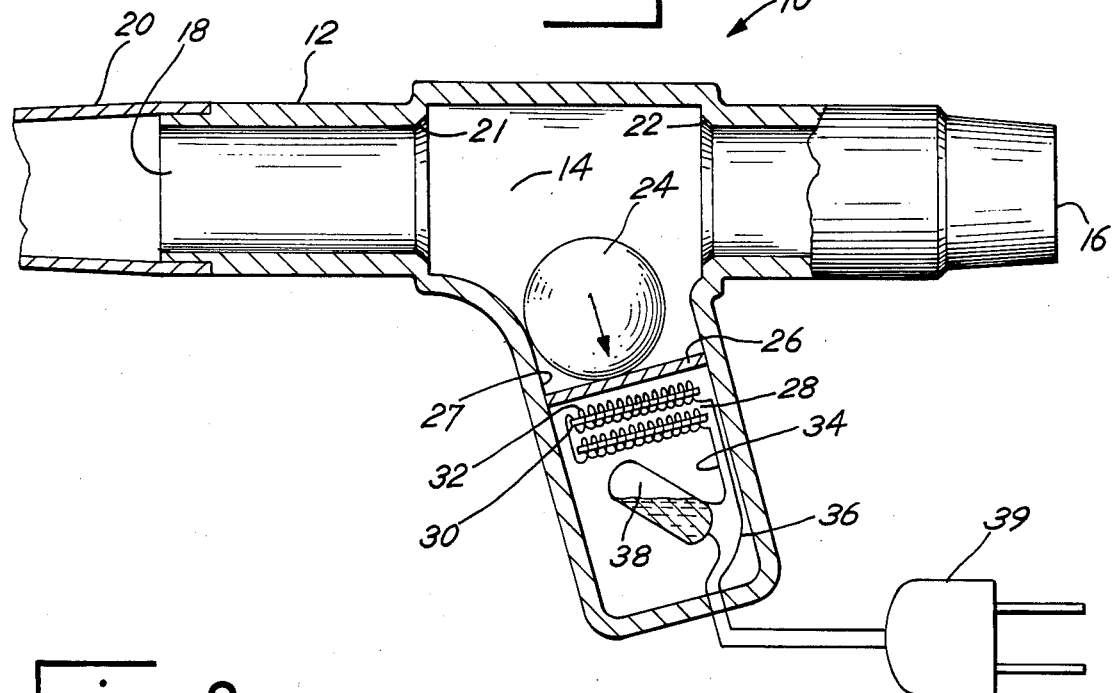
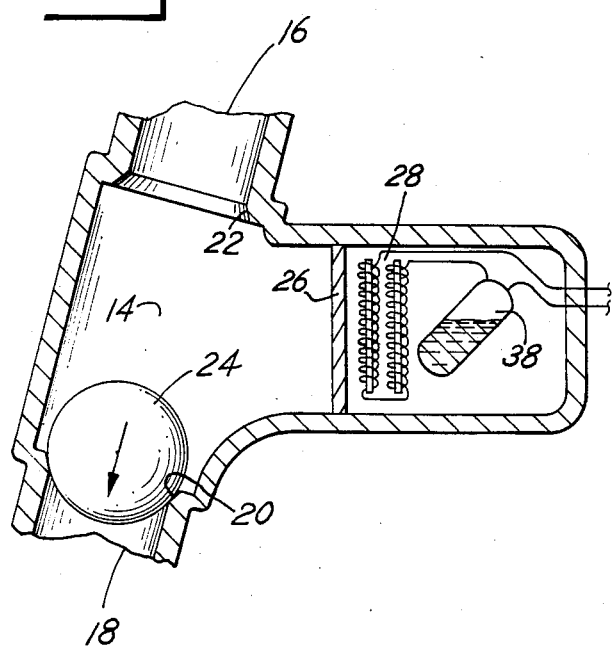
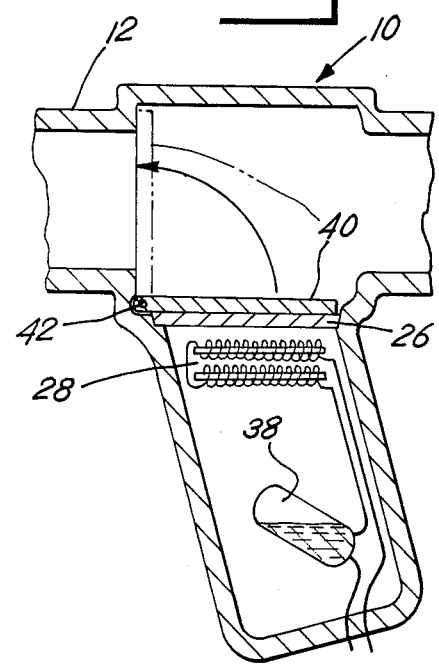

AUTOMATIC HIGH VELOCITY EVACUATOR DENTAL SUCTION DEVICE

BACKGROUND OF THE INVENTION

This invention relates to an automatic, high velocity evacuator, dental suction device. More particularly, this invention relates to a dental suction device that is easily and automatically operable.

In the practice of dentistry, the use of a suction device is often required to remove excess fluids and debris from the mouth of the dental patient. Typical such devices for this purpose include a vacuum pump or other suction source connected by tubing to a hand-held instrument having a suction nozzle with a valve for regulating the suction by the nozzle.

A disadvantage of many prior art devices is that they require manual operation of the valve, often forcing the operator to use both hands to control suction operation, thereby inhibiting effective patient treatment. Other prior art devices are equipped with slide switches or similar elements enabling them to be operated with one hand. However, such devices are susceptible to disadvantages such as leakage, premature wear and awkwardness of use.

The present invention overcomes the recited disadvantages of the prior art. The disclosed dental suction device operates automatically, freeing the operator's hands and attention for more effective and efficient patient care. Leakage and wear are reduced because no moving parts communicate between the interior and exterior of the device.

SUMMARY OF THE INVENTION

A principal object of the present invention is to provide an improved dental suction device easily and automatically operable by the user.

A further object of the invention is to provide an improved dental suction device operationally responsive to orientation of the hand held portion of the device.

Another object of the present invention is to provide an improved dental suction device which is long-wearing and less susceptible to leakage.

These and other important objects are achieved by the invention, which is, in a principal aspect, an improved automatically operable, dental suction device. The device includes, in combination, a suction line connected to a hand held suction nozzle with an orientation-responsive switch adapted to control a valve in the suction line and thus regulate the suction applied through the device. The switch operates to open the valve thereby permitting suction of fluid and debris when oriented in a first operating position, and closes the valve to prevent such suction flow when the switch is oriented in a second standby position. In a preferred embodiment, the switch is adapted to operate a magnetically responsive valve member disposed within the suction line, thereby allowing the vacuum pump or other suction source to be operated continuously.

BRIEF DESCRIPTION OF THE DRAWINGS

FIG. 1 is a side, cross-sectional view of a preferred embodiment of the improved dental suction device of the present invention in a first, operational orientation.

FIG. 2 is a side, cross-sectional view of the preferred embodiment of the invention in a second, standby orientation.

FIG. 3 is a cross-sectional side view of an alternative construction of the invention.

DETAILED DESCRIPTION OF THE DRAWINGS

Referring to the drawings, FIG. 1 illustrates a first preferred embodiment of the invention. An automatic, high velocity evacuator, dental suction device 10 includes a hand-held instrument 12 having a throughbore 14 with an inlet 16 and an outlet 18. The outlet 18 is adapted for connection to tubing 20 leading to a vacuum pump, evacuator or other suction source (not shown). The inlet 16 is preferably in the form of a standard nozzle or is adapted for connection to a standard dental suction tip (not shown).

Positioned in the throughbore 14, intermediate the inlet 16 and the outlet 18, is a valve mechanism. The valve mechanism includes a valve member 24, which is made from a magnetic material. Valve member 24 is preferably a ball member sized to be both freely movable within throughbore 14 and capable of forming a seal with seats 21, 22 within the throughbore 14. Thus, seats 21, 22 comprise spaced, circumferential sealing ribs on the inside of the cylindrical throughbore. When the ball valve member 24 is seated on a seat 21, 22, a seal is formed preventing fluid flow in the throughbore 14.

Normally, the valve member 24 is sealed on seat 21 when suction is provided for the device (FIG. 2). Thus, when the device 10 is oriented in a standby position, the ball valve member 24 is held by suction in a sealing position with seat 21 within the throughbore 14. The forward rib member 22 normally prevents the ball valve member 24 from escaping from the throughbore 14 when there is no suction.

The suction device 10 also includes an electromagnetic actuator including a plate 26, which is preferably sealed in place in a side passage 27 connected to throughbore 14. Plate 26 is juxtaposed or backed by an electromagnetic coil 28, comprising at least one core 30 and windings 32. Electromagnetic coil 28 is connected by wires 34, 36 through a mercury switch 38 to an appropriate power supply (not shown) via plug 39. Mercury switch 38 is disposed within the device 10 so as to be operationlly responsive to the orientation of the device 10.

FIG. 1 shows the device 10 in a first operational position. In use orientation of the device 10 in this first operational position permits electricity to flow through the mercury switch 38 to electromagnet 28. This electric current causes an electromagnetic force to be generated at electromagnetic plate 26. The force acts upon ball valve member 24, overcoming the force created by the vacuum formed at the seal 21 and causing ball valve member 24 to move into passage 27 toward electromagnetic plate 26. The valve mechanism is thereby opened, permitting excess fluids and debris to pass into inlet 16, through the throughbore 14 of the device 10 and out outlet 18.

As previously noted, FIG. 2 shows the device 10 in a second or standby position. Orientation of the device 10 in this second or standby position deactivates mercury switch 38, stopping the flow of electric current to electromagnetic coil 28 and interrupting the electromagnetic force generated at electromagnetic plate 26. Ball valve member 24, no longer attracted by the electromagnetic force, is returned by suction to a sealing position with seal or rib 21.

A second preferred embodiment of the invention is shown in FIG. 3. There a metallic flap 40 is hinged on a rib 42 to define a valve within the throughbore 14. Metallic flap 40 occupies a sealing position when the device 10 is oriented in a second or standby position, i.e., when the mercury switch 38 is open. Reorientation of mercury switch 38 to the first operational position of FIG. 3 causes an electromagnetic force to be generated at electromagnetic plate 26. The electromagnetic force attracts the metallic flap 40, causing it to pivot toward the plate 26. This rotation opens the valve mechanism and permits flow of fluid and debris from the inlet 16 through the throughbore 14 of the device 10 to outlet 18. In contrast, orientation of the device 10 to the second or standby position interrupts the flow of electric current in coil 30 and the electromagnetic force terminates, allowing metallic flap 40 to be returned by suction to a sealing position.

Thus, a novel and improved dental suction device has been disclosed. While first and second preferred embodiments have been described in detail, it will be apparent to those skilled in the art that changes can be made without departing from the scope of the invention.

What is claimed is:

1. In a dental suction device of the type including a hand-held instrument with a throughbore having an inlet and an outlet, suction means connected to the outlet, and valve means for controlling fluid flow in the throughbore, the improvement comprising an orientation responsive switch means integral with the hand-held instrument for controlling the valve means and adapted to operate the valve means to permit suction of fluid and debris when aligned in a first operating position, and to prevent such suction and flow when said switch is aligned in a second standby position.

2. The dental suction device of claim 1 wherein said orientation-responsive switch means comprises a mercury switch.

3. An automatic, high velocity evacuator, hand-held dental suction device comprising, in combination:
   a suction line having an inlet and an outlet, said outlet being connected by tubing means to a vacuum pump or other suction source, and said inlet being adapted for connection to a standard dental suction tip;
   a throughbore within the suction line;
   valve means comprising a magnetic material freely movable within the throughbore and adapted to define a blocking member and form a seal within the suction line;
   electromagnet means for exerting an attractive force upon said blocking member sufficient to cause movement of the blocking member toward a source of the electromagnetic force to open the throughbore;
   orientation responsive switch means integral with the device and adapted to close an electrical circuit, and energize said electromagnet means, said orientation responsive switch positioned in a first operating position, and said orientation responsive switch means being adapted to deenergize said electromagnet means when the device is positioned in a second standby position.

4. The dental suction device of claim 3 wherein said valve means comprises a metallic flap.

5. The device of claim 3 wherein said switch means is a mercury switch.

* * * * *